United States Patent
Lemke et al.

(10) Patent No.: US 6,755,195 B1
(45) Date of Patent: Jun. 29, 2004

(54) DEVICE FOR CONTROLLING AN ELECTRIC APPLIANCE USED IN THE STERILE AREA DURING MEDICAL OPERATIONS

(76) Inventors: Norbert Lemke, Danziger Str. 11, D-82194, Gröbenzell (DE); Rosemarie Lemke, Danziger Str. 11, D-82194, Gröbenzell (DE)

( * ) Notice: Subject to any disclaimer, the term of this patent is extended or adjusted under 35 U.S.C. 154(b) by 199 days.

(21) Appl. No.: 09/869,847
(22) PCT Filed: Nov. 10, 2000
(86) PCT No.: PCT/EP00/11130
§ 371 (c)(1),
(2), (4) Date: Oct. 18, 2001
(87) PCT Pub. No.: WO01/34052
    PCT Pub. Date: May 17, 2001

(30) Foreign Application Priority Data

Nov. 11, 1999 (DE) .......................................... 199 54 497

(51) Int. Cl.$^7$ ................................................. A61F 5/37
(52) U.S. Cl. ..................................... 128/849; 128/853
(58) Field of Search ................................. 128/849–856

(56) References Cited

U.S. PATENT DOCUMENTS 6,491,701 B2 * 12/2002 Tierney ...................... 606/130

FOREIGN PATENT DOCUMENTS

FR 2 671 507 1/1991 ............ B25J/13/02

* cited by examiner

Primary Examiner—Michael A. Brown
(74) Attorney, Agent, or Firm—Antonelli, Terry, Stout & Kraus, LLP

(57) ABSTRACT

The invention is a device for application in the sterile area for controlling an electric instrument provided in the non-sterile area, with the sterile area being separated from the non-sterile area substantially by a covering. The invention comprises at least one sensor responsive to the magnetic field which is provided in the non-sterile area and a unit generating a magnetic field is provided in the sterile area. The at least one sensor responsive to the magnetic field and the unit generating a magnetic field are separated from each other at least by the covering. The unit generating the magnetic field is disposed relative to the at least one sensor responsive to a magnetic field so that a variation of the magnetic field in space and/or time, which is induced by the unit generating the magnetic field, is detectable by the at least one sensor responsive to the magnetic field and a sensor signal can be generated. A controller unit is provided that generates a control signal for controlling the electric instrument in response to the sensor signal.

25 Claims, 1 Drawing Sheet

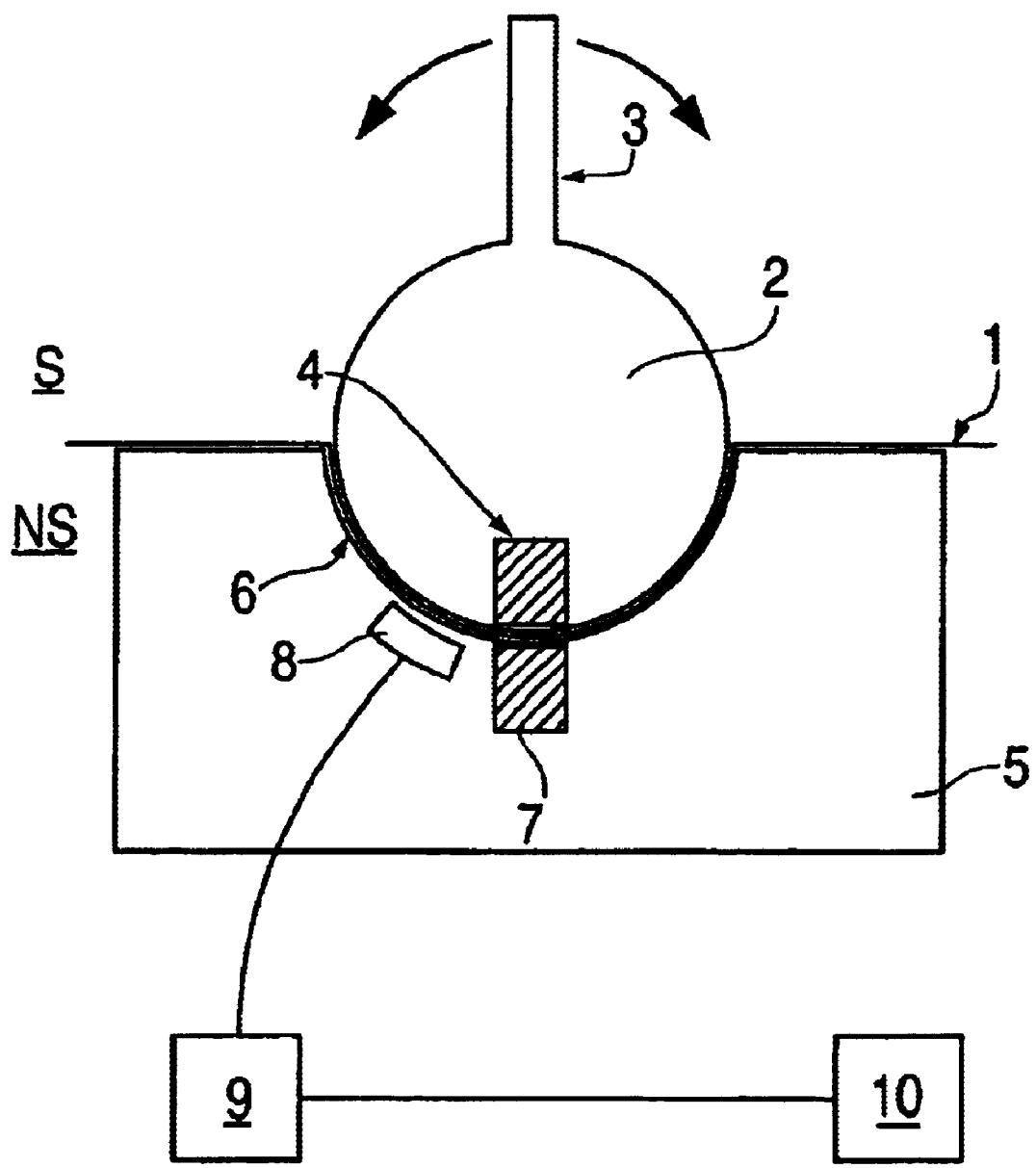

DEVICE FOR CONTROLLING AN ELECTRIC APPLIANCE USED IN THE STERILE AREA DURING MEDICAL OPERATIONS

BACKGROUND OF THE INVENTION

1. Field of the Invention

The invention relates to a device for application in the sterile area for controlling an electric instrument provided in the non-sterile area, with the sterile area being separated from the non-sterile area substantially by a sheet-like covering means.

2. Description of the Prior Art

When surgical operations are performed on both the human body and an animal body, instruments driven by electromotor force are required to an ever-increasing extent for the purposes of assisting the surgical operation and for monitoring the operation, such as holding and positioning mechanisms of a tripod- or support-like configuration for endo-surgical instruments as well as for optical monitoring and recording units such as video cameras. For reasons of easier handling and for avoidance of monotonous long-lasting positioning operations such as optical endoscope viewing systems to which a video camera unit is connected, the surgeon mostly places the system in a position ideal for performance of the operation via an appropriate positioning mechanism with electromotor support. Such a motor-drive fixing device or positioning device is described in the German Patent DE 199 50 440.

In alt known electrically controllable devices serving for assistance in surgery, which the staff must operate, the fundamental problem of operability arises, specifically as the surgeon involved in the surgical operation works with both hands in the sterile area.

When surgical operations are performed on a patient, the sterile area is limited by the clinical covering sheet lying on the patient, which consists normally of a sterilized textile or cotton tissue. The surgical operation to be performed on the patient is carried out through an opening inside the covering sheet. All objects located above the covering sheet must therefore be sterilized whereas the objects located underneath the covering sheet or at a fairly wide spacing from the surgical event need not be sterile or at least not freed from germs by 100%.

Any manual direct operation or control of electric instruments located in the non-sterile area is therefore impossible for the surgeon for reasons of sterility Pedal-operable control units disposed underneath an operating table, which provide for the surgeon a possibility to generate appropriate control signals via pedal contact switches or similar switching mechanisms, constitute a practical self-suggesting operating possibility for the surgeon. Such switch units for pedal operation present, however, fundamental disadvantages, specifically since they are not in the surgeon's range of view. When certain electric instruments used to assist the operation should not only be switched on and off but also be operated individually, such as changes of the sense of rotation of a rotational drive or when the rotational speed is to be varied, this requires a great number of pedal switches to be operated in different ways, whose operability becomes less and less easy to survey for the surgeon as the number increases.

Another possibility of operating electric instruments from the sterile area also in the non-sterile area is the application of remote controllers of the kind known also for controlling conventional TV sets. Such battery-operated control panels can be expediently operated by the surgeon by hand, provided that they are entirely sterilizable, and may be placed in the sterile area immediately within the range of vision of a surgeon. What is a disadvantage, however, is the operation from a battery that provides only limited power supply. When the power supply is exhausted exactly during performance of an operation on account of the limited battery capacity, the electric instruments important for the operation can no longer be used for the operation. A diligent and permanent servicing of such remote control panels is accordingly indispensable. In view of the communication technology, which is mostly based on infrared or ultrasonic waves, it is moreover necessary for trouble-free communication between the remote controller and the electric instrument to be controlled that an unrestricted viewing contact exists between the remote commander and the electric instrument to be controlled. Whenever there are obstacles along the path, for example, in the form of persons control is strongly impaired or even impossible.

The French publication FR 2 671 507 discloses a sample table for biomedical samples, which can be positioned in the x-y direction by means of a manual operating panel present in the non-sterile zone of the room.

U.S. Pat. No. 5,969,502 describes a joystick system including a ferromagnetic track ball adapted to be moved relative to two sensor elements. The sensor elements are now capable of detecting the movements of the track ball so that joystick control becomes possible. The known joystick system is, however, unsuitable for the sterile application in the surgery zone.

SUMMARY OF THE INVENTION

The present invention provides a device for application in the sterile area for controlling an electric instrument provided in the non-sterile area, with the sterile area being separated from the non-sterile area substantially by a sheet-like covering means, of the kind in which the aforementioned disadvantages of the solutions are known. In particular, the device is easy to operate and maintenance-free in particular. A surgeon should have the possibility to issue control commands to the electric instrument to be controlled by manual operation in the sterile area, without exposure to the risk of contamination originating from the non-sterile area.

In accordance with the invention, a device for the application in the sterile area for controlling an electric instrument provided in the non-sterile area, with the sterile area being separated from the non-sterile area substantially by a sheet-like covering means, is improved by the provision that at least one sensor responsive to a magnetic field is provided in the non-sterile area and a unit generating a magnetic field is provided in the sterile area. The sensor responsive to a magnetic field as well as the unit generating the magnetic field are separated from each other at least by the sheet-like covering means, with the unit responsive to the magnetic field being disposed relative to the sensor responsive to the magnetic field being disposed in such a way that a variation in terms of space and/or time of the magnetic field created by the unit generating the magnetic field can be detected by the sensor responsive to the magnetic field and a sensor signal can be generated, and that finally a control unit is provided which generates a control signal for controlling the electric instrument in response to the sensor signal.

The device of the invention utilizes receives the control signals generated by the surgeon by means of magnetic interaction through the surgical towel or drape, that is from the sterile area into the non-sterile area, with the sheet-like covering means, i.e. the surgical sheet present in any operation, becoming part of the device as such.

In the simplest embodiment of the inventive device, according to the invention a permanent magnet is provided in the sterile area, which can be manually operated by the surgeon and must therefore be realized in a sterilizable form. A Hall sensor or a similar sensor responsive to a magnetic field, which detects variations in the magnetic field, generates sensor signals which are converted by means of an appropriately configured control unit into control signals for direct control of an electric instrument.

In order to establish a spatially fixed relationship between the unit generating the magnetic field and the sensor responsive to the magnetic field, which is located underneath the sheetlike covering means in the sterile zone, both components are integrated into appropriate molded bodies which are mobile relative to each other via appropriately configured contours in a spatially fixed relationship. For example, the unit generating the magnetic field, which is configured as permanent magnet or solenoid, is located in an operating element having a spherical configuration, which is separated by the sheet-like covering means and can be placed in an appropriately configured basic body having a semi-spherical counter-shape as well as the sensor responsive to the magnetic field. The two components can be moved relative to each other via the spherically shaped contact area between the operating element and the basic body.

The basic body, in which the sensor is responsive to the magnetic field, preferably comprises additionally an insert of ferromagnetic material or a counter-magnet selected in correspondence with the unit generating the magnetic field so that when the operating element is inserted into the basic body both components fit into each other in a self-centering manner. When the surgeon deflects the operating element in the sterile area from a centered position to the side, the sensor responsive to the magnetic field is capable of detecting the variation of the magnetic field, that derives from the deflection, which results in the generation of a corresponding control signal. When the surgeon releases grip on the operating element, the instrument returns automatically into an original position.

Moreover, an installation of the control device in accordance with the invention in the immediate vicinity of the operating area on the surgical towel or drape is easy to carry out. It is merely necessary to position the basic body under the sheet-like covering means and to insert the operating element into the basic body appropriately from the sterile side of the covering sheet, with the inserting operation being facilitated by the counter-magnet provided in the basic body and the permanent magnets disposed in the operating element.

BRIEF DESCRIPTION OF THE DRAWING

The invention will be described hereinbelow by an exemplary embodiment, without any restriction of the general inventive idea, with reference to the drawing wherein:

FIG. 1 is a schematic cross-sectional view taken through a controller device.

DESCRIPTION OF THE PREFERRED EMBODIMENTS

FIG. 1 illustrates a schematic cross-sectional view taken through a controller device. The sheet-like covering means 1 separates the sterile area S from the non-sterile area NS. In the sterile region S, which the surgeon can reach manually without any problem during the performance of a surgical operation, an operating element 2 is provided that has a circular cross-section. Based on principle, operating elements having a cylindrical or spherical configuration are suitable. For a simple operation of the operating element 2, the operating element is provided with an operating lever 3 which the surgeon can easily grasp and pivot in the direction indicated by the illustrated arrow. A permanent magnet 4 is inserted into the operating element on the underside thereof.

A basic body 5 is provided in the non-sterile area NS, that is separated by the sheet-like covering means and is provided with a recess 6 adapted as counter-contour to the circular geometry of the operating element 2. In the event that the operating element is configured in the form of a cylinder, an operative connection is established between the operating element 2 and the basic body 5 via a semi-cylindrical contact area. Moreover, the basic body 5 is provided with a permanent magnet 7 that is disposed with opposite polarization relative to the permanent magnet 4. The operating element 23 and the basic body automatically center themselves due to the magnetic forces acting between the permanent magnets 4 and 5, without any further outside moment of force being required. Apart from the permanent magnet 7, a Hall element 8 is provided in the basic body 5, which detects the magnetic fields and particularly variations of the magnetic field prevailing in the environment. The Hall element 8 is connected to a controller unit 9 which converts the sensor signals into control signals by means of which an electric instrument 10 can be selectively controlled.

When the surgeon now pivots the operating element 2 by means of the operating lever 3 in a defined direction, the permanent magnet 4 is moved relative to the Hall sensor 8, which results in a variation of the magnetic field in terms of time and generates a sensor signal. This signal is converted by the control unit into a corresponding control signal serving to control the electric instrument 10.

When the surgeon releases his grip on the operating element 2 deflected in one direction, the operating element moves automatically back into its initial position, as illustrated in FIG. 1.

It is, of course, also possible to integrate several Hall sensors into the basic body 5 for reasons of optimization of the sensor signals so that, for example, a pivoting movement of an operating element configured as a sphere into any and all three-dimensional directions results in correspondingly differentiated sensor signals suitable for being converted by the controller unit 9 into discrete control signals. For example, the surgeon can use the operating lever 3 as some kind of joystick in order to achieve a maximum precision, for example, in positioning a holding tripod or support on which endo-surgical instruments are mounted.

Due to the simple structure of the device and particularly on account of the fact that systems requiring electrical energy are entirely avoided in the sterile area, the device may be deemed to be completely maintenance-free. Moreover, the installation of the inventive controller unit is very easy to perform also for the surgeon, specifically as the surgeon must position the basic body at a suitable position under the operation drape and must merely position the sterile operating element above the operation drape in the corresponding counter-contour in the basic body. As the operating element presents a plain geometry and consists entirely of a material suitable for autoclaving, the operating element is easily sterilizable with the conventional sterilization techniques. For example, permanent magnet materials are presently available whose Curie temperature ranges far above 300°, that is in a temperature range by far higher than the range that is required for a complete sterilization of objects.

Moreover, the device permits a displacement relative to the operation drape during the operation because the operation drape can pass along the contact area between the operating Depending on the number of the control commands to be issued by the surgeon, the basic body may be provided with multiple provisions for accommodating individual separate operating element which are all adapted to be inserted into a single basic body. In order to be able—in the case of two or more operating elements to achieve a correct unambiguous assignment between the basic body, which is located under the operation drape and is not visible to the surgeon, the upper side of the basic body presents contours which the surgeon can detect by touching and which enable the surgeon to equip the basic body correctly with a corresponding variety of operating elements in the correct arrangement. The operating elements are preferably manufactured of metal or similar materials easy to sterilize may offer to the surgeon easily detectable possibilities of distinction by different color and/or shaping, which enable the surgeon to select an easier correlation between different control commands and the respective operating elements.

In addition to the aforedescribed toggle switch described in the embodiment with reference to FIG. 1, it is also possible to generate an analog control signal with the operating element. To this end, further permanent magnets must be disposed circularly around the central permanent magnets 4 within the operating element. When the operating element is now rotated about the central permanent magnet 4, the individual permanent magnets in circular arrangement travel in succession over the Hall sensor suitable to generate analog control signals in a manner comparable to a potentiometer. These signals may be used, for example, for dimming a lighting fixture.

LIST OF REFERENCE NUMERALS 1 sheet-like covering means
2 operating element
3 operating lever
4 permanent magnet
5 basic body
6 outside contour
7 permanent magnet
8 Hall sensor
9 controller unit
10 electrical instrument

What is claimed is:

1. A device for application in a sterile area for controlling an electric instrument provided in a non-sterile area, with the sterile area being separated from the non-sterile area substantially by a covering, wherein:
   at least one sensor responsive to the magnetic field is provided in the non-sterile area and a unit generating a magnetic field is provided in the sterile area, the at least one sensor responsive to the magnetic field and the unit generating a magnetic field are separated from each other at least by the covering means,
   the unit generating the magnetic field is disposed relative to the at least one sensor responsive to a magnetic field so that a variation of the magnetic field in space and/or time, which is induced by the unit generating the magnetic field, is detectable by the sensor responsive to the magnetic field and a sensor signal is generated, and controller unit is provided that generates a control signal for controlling the electric instrument in response to the sensor signal.

2. A device according to claim 1, wherein the unit generating a magnetic field is a permanent magnet or a solenoid.

3. A device according to claim 2, wherein the magnetic field generated by the unit generating a magnetic field presents a three-dimensional extension corresponding approximately to a size of the at least one sensor responsive to the magnetic field.

4. A device according to claim 2, wherein the unit generating a magnetic field is integrated into an operating element comprising a non-magnetic material;
   the at least one sensor responsive to the magnetic field is integrated into a body comprising a non-magnetic material; and
   the operating element and the body include contour areas presenting corresponding configurations relative to each other in such a way that the operating element enters, at least partly, into an operative interaction with the body via a plane or curved contact area, separated by the covering.

5. A device according to claim 4, wherein a contact surface of the body presents a concave shape to which the contact surface of the operating element with a convex shape is matched.

6. A device according to claim 4, wherein a contact surface of the body and the operating element present a semi-cylindrical or spherical shape.

7. A device according to claim 4, wherein a contact surface of the body and the operating element present a semi-cylindrical or spherical shape.

8. A device according to claim 1, wherein the magnetic field generated by the unit generating a magnetic field presents a three-dimensional extension corresponding approximately to a size of the at least one sensor responsive to the magnetic field.

9. A device according to claim 8, wherein the unit generating a magnetic field is integrated into an operating element comprising a non-magnetic material;
   the at least one sensor responsive to the magnetic field is integrated into a body comprising a non-magnetic material; and
   the operating element and the body include contour areas presenting corresponding configurations relative to each other in such a way that the operating element enters, at least partly, into an operative interaction with the body via a plane or curved contact area, separated by the covering.

10. A device according to claim 9, wherein a contact surface of the body presents a concave shape to which a contact surface of the operating element with a convex shape is matched.

11. A device according to claim 9, wherein a contact surface of the body and the operating element present a semi-cylindrical or spherical shape.

12. A device according to claim 9, wherein a contact surface of the body and the operating element present a semi-cylindrical or spherical shape.

13. A device according to claim 1, wherein the unit generating a magnetic field is integrated into an operating element comprising a non-magnetic material;
   the at least one sensor responsive to the magnetic field is integrated into a body comprising a non-magnetic material; and the operating element and the body include contour areas presenting corresponding configurations relative to each other in such a way that the operating element enters, at least partly, into an operative interaction with the body via a plane or curved contact area, separated by the covering.

14. A device according to claim 13, wherein a ferromagnetic element or a counter-magnet relative to the unit generating a magnetic field is provided in the body so that the operating element and body joinable in a self-centering manner such that the ferromagnetic element or the counter-magnet is positioned directly opposite the unit generating the magnetic field.

15. A device according to claim 14, wherein a plurality of units generating a magnetic field are disposed in a circular arrangement in the body relative to the ferromagnetic element or counter-magnet, and/or additional units generating a magnetic field are provided in the operating element, in a circular arrangement relative to the unit generating a magnetic field so that by rotation of the operating element about a central unit generating a magnetic field, relative to the body, control signals are generated in the at least one sensor responsive to the magnetic field, which generate analog control signals.

16. A device according to claim 14, wherein a contact surface of the body presents a concave shape to which a contact surface of the operating element with a convex shape is matched.

17. A device according to claim 16, wherein a plurality of units generating a magnetic field are disposed in a circular arrangement in the body relative to the ferromagnetic element or counter-magnet, and/or additional units generating a magnetic field are provided in the operating element, in a circular arrangement relative to the unit generating a magnetic field so that by rotation of the operating element about the central unit generating a magnetic field, relative to the body, control signals are generated in the at least one sensor responsive to the magnetic field, which generate analog control signals.

18. A device according to claim 14, wherein a contact surface of the body and the operating element present a semi-cylindrical or spherical shape.

19. A device according to claim 18, wherein a plurality of units generating a magnetic field are disposed in a circular arrangement in the body relative to the ferromagnetic element or counter-magnet, and/or additional units generating a magnetic field are provided in the operating element, in a circular arrangement relative to the unit generating a magnetic field so that by rotation of the operating element about the central unit generating a magnetic field, relative to the body, control signals are generated in the at least one sensor responsive to the magnetic field, which generate analog control signals.

20. A device according to claim 13, wherein the contact surface of the basic body presents a concave shape to which the contact surface of the operating element with a convex shape is matched.

21. A device according to claim 20, wherein a contact surface of the body and the operating element present a semi-cylindrical or spherical shape.

22. A device according to claim 21, wherein a plurality of units generating a magnetic field are disposed in a circular arrangement in the body relative to the ferromagnetic element or counter-magnet, and/or additional units generating a magnetic field are provided in the operating element, in a circular arrangement relative to the unit generating a magnetic field so that by rotation of the operating element about the central unit generating a magnetic field, relative to the body, control signals are generated in the at least one sensor responsive to the magnetic field, which generate analog control signals.

23. A device according to claim 20, wherein a plurality of units generating a magnetic field are disposed in a circular arrangement in the body relative to the ferromagnetic element or counter-magnet, and/or additional units generating a magnetic field are provided in the operating element, in a circular arrangement relative to the unit generating a magnetic field so that by rotation of the operating element about the central unit generating a magnetic field, relative to the body, control signals are generated in the at least one sensor responsive to the magnetic field, which generate analog control signals.

24. A device according to claim 13, wherein the contact surface of the body and the operating element present a semi-cylindrical or spherical configuration.

25. A device according to claim 24, wherein a plurality of units generating a magnetic field are disposed in a circular arrangement in the body relative to the ferromagnetic element or counter-magnet, and/or additional units generating a magnetic field are provided in the operating element, in a circular arrangement relative to the unit generating a magnetic field so that by rotation of the operating element about the central unit generating a magnetic field, relative to the body, control signals are generated in the at least one sensor responsive to the magnetic field, which generate analog control signals.

* * * * *